US011232857B2

(12) United States Patent
Alvelda, VII et al.

(10) Patent No.: US 11,232,857 B2
(45) Date of Patent: Jan. 25, 2022

(54) FULLY AUTOMATED NON-CONTACT REMOTE BIOMETRIC AND HEALTH SENSING SYSTEMS, ARCHITECTURES, AND METHODS

(71) Applicant: Brainworks Foundry, Inc., Arlington, VA (US)

(72) Inventors: Phillip Alvelda, VII, Arlington, VA (US); Markus Krause, Oakland, CA (US); Zvi Huber, Great Falls, VA (US); Todd Allen Stiers, Berkeley, CA (US); Aleksandra Joanna Sokolowska, Zug (CH)

(73) Assignee: Brainworks Foundry, Inc., Arlington, VA (US)

( * ) Notice: Subject to any disclaimer, the term of this patent is extended or adjusted under 35 U.S.C. 154(b) by 0 days.

(21) Appl. No.: 16/590,000

(22) Filed: Oct. 1, 2019

(65) Prior Publication Data
US 2020/0105400 A1  Apr. 2, 2020

Related U.S. Application Data

(60) Provisional application No. 62/739,365, filed on Oct. 1, 2018, provisional application No. 62/739,924, filed on Oct. 2, 2018.

(51) Int. Cl.
*G16H 30/40* (2018.01)
*G06F 9/54* (2006.01)
(Continued)

(52) U.S. Cl.
CPC .............. *G16H 30/40* (2018.01); *G06F 9/544* (2013.01); *G06K 9/00288* (2013.01);
(Continued)

(58) Field of Classification Search
CPC ........ G16H 30/40; G16H 40/63; G16H 50/20; G06F 9/544; G06F 9/505; G06K 9/00288;
(Continued)

(56) References Cited

U.S. PATENT DOCUMENTS 5,634,037 A    5/1997  Sasaki et al.
8,538,775 B2 *  9/2013  Skomra .................. G16H 20/10
                                                                705/3
(Continued)

FOREIGN PATENT DOCUMENTS

JP    4472273 B2    6/2010
JP    4725964 B2    7/2011

OTHER PUBLICATIONS

International Search Report and Written Opinion in International Application No. PCT/US2019/054090 dated Dec. 18, 2019.

*Primary Examiner* — Juan A Torres
(74) *Attorney, Agent, or Firm* — Greenberg Traurig, LLP; Chinh H. Pham; Kristopher Reichlen (57) ABSTRACT

Systems and methods for fully-automated contact-less biometric measurement include receiving a stream of image frames from an internet capable device. Frame data is extracted from the stream of image frames. A predictive load balancer selects a worker server based on a load prediction. An interface delivery server communicates the frame data from the internet capable device to the worker server. A set of patient face images captured by the frame data are extracted. A facial recognition machine learning model determines a patient identity associated with the set of patient face images of the frame data. A shared memory system stores the set of patient face images. The worker server determines biometric measurements based on the set of patient face images in the shared memory system using independent biometric data processing pipelines with shared
(Continued)

access to the shared memory system for inter-process communication.

20 Claims, 6 Drawing Sheets

(51) Int. Cl.
    *G06K 9/00*    (2006.01)
    *G06T 7/00*    (2017.01)
    *G06N 20/00*    (2019.01)

(52) U.S. Cl.
    CPC ........... *G06N 20/00* (2019.01); *G06T 7/0012* (2013.01); *G06T 2207/30201* (2013.01)

(58) Field of Classification Search
    CPC ........... G06K 2009/00939; G06K 9/34; G06K 9/00744; G06T 7/0012; G06T 2207/30201; G06N 20/00; G06N 20/20; G06N 5/003; G06N 3/0454; G06N 3/088
    USPC ........................................................ 382/118
    See application file for complete search history.

(56) References Cited

U.S. PATENT DOCUMENTS

| | | |
|---|---|---|
| 2002/0019844 A1 | 2/2002 | Kurowski et al. |
| 2007/0180261 A1 | 8/2007 | Akkermans et al. |
| 2009/0067726 A1 | 3/2009 | Erol et al. |
| 2009/0074259 A1 | 3/2009 | Baltatu et al. |
| 2010/0228692 A1 | 9/2010 | Guralnik et al. |
| 2011/0249742 A1 | 10/2011 | Price et al. |
| 2013/0243329 A1 | 9/2013 | Garcia et al. |
| 2016/0154991 A1* | 6/2016 | Berini ................. G06F 21/6245 382/116 |
| 2016/0294825 A1 | 10/2016 | Nice et al. |
| 2016/0308859 A1 | 10/2016 | Barry et al. |
| 2016/0364609 A1* | 12/2016 | Ivanisov ............... G06K 9/4604 |
| 2017/0102970 A1 | 4/2017 | Kolk et al. |
| 2017/0109570 A1* | 4/2017 | Finkelstein ............. H04L 67/10 |
| 2017/0326333 A1* | 11/2017 | Giap ........................ A61B 6/46 |
| 2019/0205615 A1* | 7/2019 | Hanina ............... G06K 9/00221 |
| 2019/0240113 A1* | 8/2019 | Velani .................... G16H 40/63 |

* cited by examiner

FULLY AUTOMATED NON-CONTACT REMOTE BIOMETRIC AND HEALTH SENSING SYSTEMS, ARCHITECTURES, AND METHODS

CROSS-REFERENCE TO RELATED APPLICATION(S)

This application claims priority to, and the benefit of, U.S. Provisional Application No. 62/739,924, filed Oct. 2, 2018 and U.S. Provisional Application No. 62/739,365, filed Oct. 1, 2018 for all subject matter common to all applications. The disclosure of said provisional applications is hereby incorporated by reference in their entirety.

FIELD OF THE INVENTION

The present disclosure relates to systems and methods suitable for identifying and tracking patients through visual facial recognition. In particular, the present disclosure relates to systems and methods for automatically tracking and measuring biometric and health data of a patient using image data captured of the patient's face.

BACKGROUND

Generally, medical biometric and health sensors require direct contact with patients using wired electrodes, cuffs or probes, including, but not limited to, those used for vital sign measurement of heartbeat or pulse rate detection, heart rate variability estimation, respiration, body temperature, and blood pressure measurement. The vital sign measurement processes have been fully manual for over fifty years, and since then, have required significant manual labor of a trained nurse, technician, or doctor, some $5,000 of dedicated equipment, and roughly fifteen minutes of labor and dedicated clinic space. Most current medical biometric and health sensors also require manual entry of patient health and identity information followed by manual transcription into health records.

The complexity of these historically manual healthcare support tasks such as vital sign measurement as required by the FDA is such that no single machine learning application up until this invention has manage to automate the entire task of situating and managing a patient, properly affixing the cuffs and electrodes, initiating the electronic measurement, verifying the validity of the recorded data, and entering the data into the patient's health record. The result is a vital sign measurement procedure that has been complicated, slow, and expensive for decades. As a result, vital sign measurements are performed infrequently, usually only after a patient has a problem, leading inevitably to a reactive healthcare system.

SUMMARY

There is a need for improvements for biometric monitoring of patients. The present disclosure provides, in various embodiments solutions to address this need, in addition to having other desirable characteristics. Specifically, the present disclosure provides systems and methods that automatically identify patients and track their biometric and health data through visual computer vision detection and processing of visual and full-body images, video, and asynchronous sensor data.

In accordance with example embodiments of the present invention, a method for fully-automated contact-less biometric measurement is provided. The method includes receiving, by at least one processor, a set of image frames produced by one or more biometric sensor devices including at least one digital image capture device, extracting, by the at least one processor, a set of patient face images captured by one or more frames of the set of image frames, determining, by the at least one processor, a patient identity associated with the set of patient face images of the one or more frames of the set of image frames using a facial recognition machine learning model, storing, by the at least one processor, the set of patient face images in a shared memory system, determining, by the at least one processor, one or more biometric measurements based on the set of patient face images in the shared memory system, each of the one or more biometric measurements being determined with an independent biometric data processing pipeline with shared access to the shared memory system for inter-process communication, exporting, by the at least one processor, the one or more biometric measurements to a user database, and displaying, by the at least one processor, a selected set of the one or more biometric measurements on a screen of a user computing device in response to a user selection.

In accordance with aspects of the present invention, the method further includes determining, by the at least one processor, a consent status associated with the patient identity indicating whether consent for biometric analysis exists. The method can further include balancing, by the at least one processor, each independent biometric data processing pipeline across a plurality of worker servers using a predictive load balancer. The method can further include determining, by the at least one processor, a neural biometric data signal for each set of patient face images independently with each independent biometric data processing pipeline using a respective super-resolution neural network. The method can further include determining, by the at least one processor, a quality measurement of a respective one or more biometric measurement in each independent biometric data measurement pipeline using a respective signal template neural network of a one or more signal template neural networks.

In accordance with aspects of the present invention, the set of image frames includes frames of one or more videos, each of the one or more videos comprising five seconds in duration. The set of image frames can include the frames of a user selected subset of the one or more videos. The method can further include sharing, by the at least one processor, results between each of the one or more independent biometric data measurement pipelines via the shared memory system. The results can include one or more of the following: the respective one or more biometric measurements of the respective one or more independent biometric data measurement pipelines, a respective quality measurement of the respective one or more independent biometric data measurement pipelines, and a respective neural biometric data signal of the respective one or more independent biometric data measurement pipelines.

In accordance with example embodiments of the present invention, a method for contact-less biometric measurement is provided. The method includes receiving, by at least one processor, a stream of image frames produced by one or more biometric sensor devices including at least one internet capable device, extracting, by the least one processor, frame data from the stream of image frames comprising a plurality of images, determining, by the at least one processor, at least one worker server from a plurality of worker servers based on a future load prediction by a predictive load balancer, communicating, by the at least one processor, the frame data from the at least one internet capable device to the at least one worker server, extracting, by the at least one processor, a set of patient face images captured by the frame data, determining, by the at least one processor, a patient identity associated with the set of patient face images of the frame data using a facial recognition machine learning model, storing, by the at least one processor, the set of patient face images in a shared memory system, determining, by the at least one processor, one or more biometric measurements based on the set of patient face images in the shared memory system, each of the one or more biometric measurements being determined with an independent biometric data processing pipeline with shared access to the shared memory system for inter-process communication, exporting, by the at least one processor, the one or more biometric measurements to a user database, and displaying, by the at least one processor, a selected set of the one or more biometric measurements on a screen of a user computing device in response to a user selection.

In accordance with aspects of the present invention, the method further includes determining, by the at least one processor, a consent status associated with the patient identity indicating whether consent for biometric analysis exists. The method can further include balancing, by the at least one processor, each independent biometric data processing pipeline across a plurality of worker servers of the at least one worker server using the predictive load balancer. The method can further include determining, by the at least one processor, a neural biometric data signal for each set of patient face images independently with each independent biometric data processing pipeline using a respective super-resolution neural network. The method can further include determining, by the at least one processor, a quality measurement of a respective one or more biometric measurement in each independent biometric data measurement pipeline using a respective signal template neural network of a one or more signal template neural networks.

In accordance with aspects of the present invention, the stream of image frames includes frames of one or more videos. The frame data can include the frames of a user selected segment of the one or more videos. The user selected segment of the one or more videos can include a selection of one or more segments each comprising 5 seconds in duration. The method can further include sharing, by the at least one processor, results between each of the one or more independent biometric data measurement pipelines via the shared memory system. The results can include one or more of the following: the respective one or more biometric measurements of the respective one or more independent biometric data measurement pipelines, a respective quality measurement of the respective one or more independent biometric data measurement pipelines, and a respective neural biometric data signal of the respective one or more independent biometric data measurement pipelines.

In accordance with example embodiments of the present invention, a system for contact-less biometric measurement is provided. The system includes one or more internet connected devices configured to produce a stream of image frames produced by one or more biometric sensor devices including at least one internet capable device, and extract frame data from the stream of image frames comprising a plurality of images. The system also includes a plurality of worker servers, each worker server comprising a respective at least one processor and a respective shared memory system, a user database in communication with the plurality of worker servers and the one or more internet connected devices, and a predictive load balancer in communication with the plurality of worker servers and configured to determine at least one worker server from the plurality of worker servers based on a future load prediction. The system further includes an interface delivery server in communication with the plurality of worker servers, the predictive load balancer and the one or more internet connect devices, and configured to communicate the frame data from the at least one internet capable device to each of the predictive load balancer and the at least one worker server. The at least one processor of the at least one worker server is configured to extract a set of patient face images captured by the frame data, determine a patient identity associated with the set of patient face images of the frame data using a facial recognition machine learning model, store the set of patient face images in the shared memory system, determine one or more biometric measurements based on the set of patient face images in the shared memory system, each of the one or more biometric measurements being determined with an independent biometric data processing pipeline with shared access to the shared memory system for inter-process communication, and export the one or more biometric measurements to the user database.

In accordance with aspects of the present invention, the at least one processor of the at least one worker server is further configured to share results between each of the one or more independent biometric data measurement pipelines via the shared memory system. The results include one or more of the following: the respective one or more biometric measurements of the respective one or more independent biometric data measurement pipelines, a respective quality measurement of the respective one or more independent biometric data measurement pipelines, and a respective neural biometric data signal of the respective one or more independent biometric data measurement pipelines. The interface delivery server can be further configured to display a selected set of the one or more biometric measurements on a screen of the one or more internet connected devices in response to a user selection.

BRIEF DESCRIPTION OF THE FIGURES

These and other characteristics of the present disclosure will be more fully understood by reference to the following detailed description in conjunction with the attached drawings, in which.

DETAILED DESCRIPTION

An illustrative embodiment of the present disclosure relates to systems and methods for implementing of a new class of completely automated artificial intelligence (AI)

enhanced remote biometric sensors that can capture, log, and telemeter precision biometric and health data. In some embodiments, the biometric sensors that can capture, log, and telemeter precision biometric and health data remotely with no leads or contacts required using live or archived video streams. The biometric sensors can also operate without requiring any human time or attention. In other words, the biometric sensors of the present disclosure can act as fully automated ambient biometric sensor systems that can be used to supplement and/or replace complex manual tasks performed by hospital, clinic, and/or in-home nurses, technicians and doctors.

The biometric sensors of the present disclosure can use any combination of data capturing devices, for example, custom video cameras, infrared (IR) cameras, hyper-spectral video imagers, event-based cameras where each pixel is independent and only records when it senses a change or movement, cameras available within consumer electronic devices (including, but not limited to: mobile phones, tablets, laptops, computers, smart Televisions, webcams, etc. . . . ), etc. The data capturing devices, in conjunction with the preset disclosure, can be used to remotely detect and measure biometrics including, but not limited to, pulse rate and respiration rates as well as higher order characteristics, skin temperature, blood pressure, blood oxygenation, Meyer waves, facial expressions and emotional affect, pain level, wakefulness, motor control disorder and tremor from disease such as Parkinson's or ALS, as well as drug efficacy from behavioral and physical biomarkers.

Once vital sign and biometric signals are measured by the data capturing devices, each measurement can be analyzed for accuracy and confounding noise to determine whether it meets specified signal quality requirements, and if so, the data can automatically be logged to the consenting patient's health record. The present disclosure takes advantage of a unique combination of steps to capture data and analyze the captured data to create an improved the vital sign measurement and patient assessment process, which can replace what can be expensive manual processes at a fraction of the cost. The technical improvement provided by the present disclosure can be so dramatic, that for the same investment, hundreds of patients could be monitored continuously 24×7 for an entire month for what it used to cost to take to manually monitor measurements for a single patient one time. The present disclosure also serves to extend the Food and Drug Administration (FDA) approved vital sign measurement outside the clinic, into homes, in vehicles, and in general where patients are mobile, radically expanding access and reducing the need to come in to hospitals and clinics in order to be assessed. Altogether, the present disclosure provides the opportunity for constant and continuous health monitoring at very little cost, to the point that health trends and crises can be predicted ahead of any crisis.

FIGS. 1 through 6, wherein like parts are designated by like reference numerals throughout, illustrate an example embodiment or embodiments of improved operation for monitoring and tracking biometric data using image data, according to the present disclosure. Although the present disclosure will be described with reference to the example embodiment or embodiments illustrated in the figures, it should be understood that many alternative forms can embody the present disclosure. One of skill in the art will additionally appreciate different ways to alter the parameters of the embodiment(s) disclosed, such as the size, shape, or type of elements or materials, in a manner still in keeping with the spirit and scope of the present disclosure.

Figure 1:
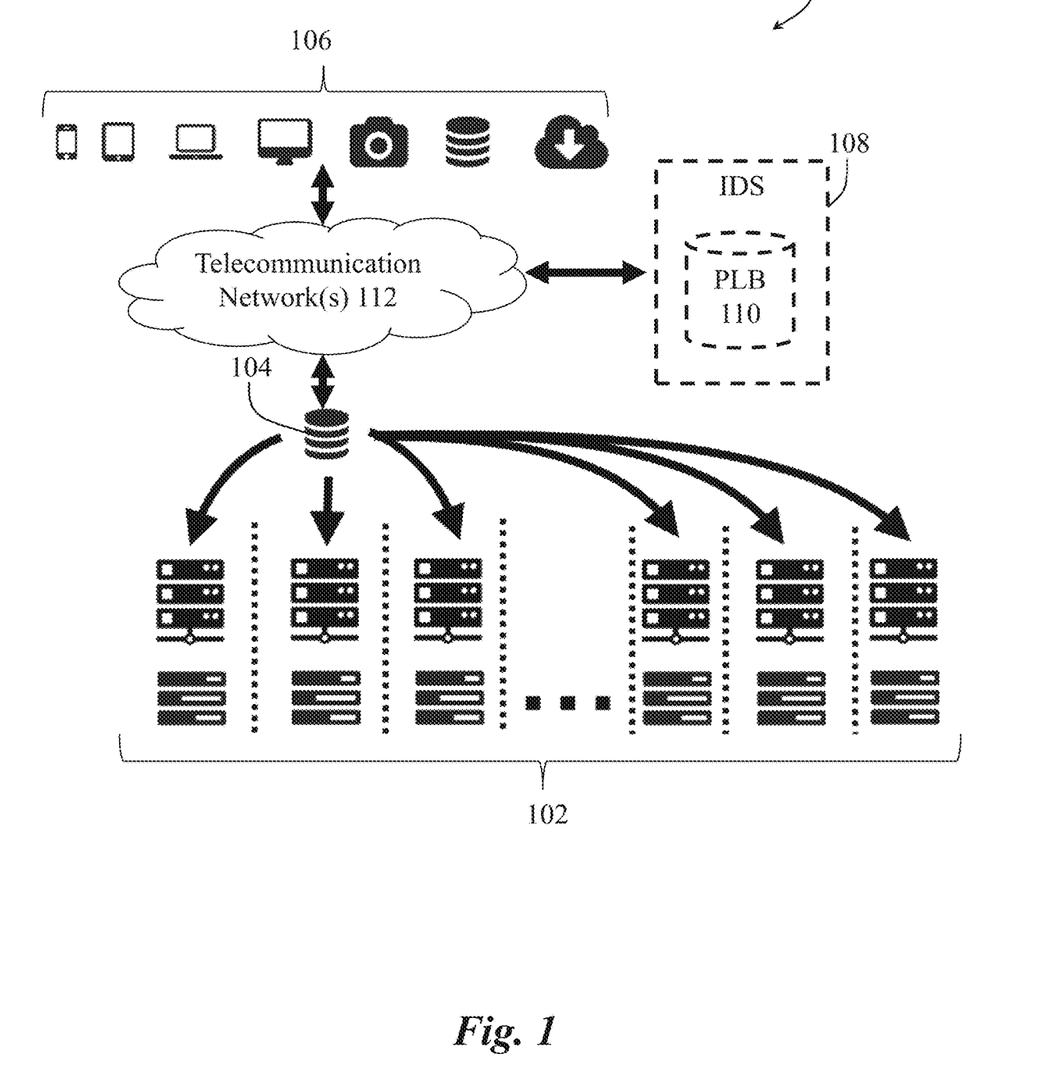
FIG. 1 is a diagrammatic illustration of a system for implementation of the methods in accordance with the present disclosure.

Referring to FIG. 1, an example fully automated biometric monitoring system 100 for implementing the present disclosure is depicted. Specifically, FIG. 1 depicts an illustrative system 100 for implementing the steps in accordance with the aspects of the present disclosure. In some embodiments, the system 100 can be a combination of hardware and software configured to carry out aspects of the present disclosure. For example, the system 100 can include a complex distributed client server architecture. In some embodiments, the system 100 can include a combination of computing devices 102. For example, the computing devices 102 can be work servers with specialized software and databases designed for providing a method for monitoring and tracking biometric data using image data. For example, the system 100 can be software installed on a computing device 102, a web based application provided by a computing device 102 which is accessible by computing devices (e.g., biometric sensor devices 106), a cloud based application accessible by computing devices, or the like. In some embodiments, the system 100 can include a cluster of computing devices 102 designed to operate in parallel. As would be appreciated by one skilled in the art, the computing device 102 can include a single computing device, a collection of computing devices in a network computing system, a cloud computing infrastructure, or a combination thereof. The combination of hardware and software that make up the system 100 are specifically configured to provide a technical solution to a particular problem utilizing an unconventional combination of steps/operations to carry out aspects of the present disclosure. In particular, the system 100 is designed to execute a unique combination of steps to provide a novel approach to monitoring and tracking biometric data and health data.

In some embodiments, the system 100 can include a storage system 104 communicatively attached to the computing device(s) 102. The storage system 104 can include any combination of computing devices configured to store and organize a collection of data. For example, storage system 104 can be a local storage device on the computing device 102, a remote database facility, or a cloud computing storage environment. The storage system 104 can also include a database management system utilizing a given database model configured to interact with a user for analyzing the database data.

In some embodiments, the system 100 can include a plurality of biometric sensor devices 106. The plurality of biometric sensor devices 106 can be any combination of internet capable devices (ICD) capable of being able to communicate with the computing device(s) 102 and/or the storage system 104. For example, the biometric sensor devices 106 can be part of and/or connected to any ICD device that can establish a connection to another device over a communication medium using connection methods, including but are not limited to, protocols such as HyperText Transfer Protocol (HTTP)/HyperText Transfer Protocol Secure (HTTPS), Transmission Control Protocol (TCP)/User Datagram Protocol (UDP), etc. Using the connection, the computing device(s) 102 and/or the storage system 104 can act as a host (centralized or distributed), for the biometric sensor devices 106, providing the functionality of the present disclosure.

In some embodiments, biometric sensor devices 106 can include a camera or other image capturing device. The camera can include any combination of devices that can record image data and/or allows transfer of image data to an internet capable device (ICD). For example, examples of cameras can include mobile phone cameras, closed-circuit television (CCTV) systems, cameras integrated in laptops tablets, personal computers, photo and video cameras, external webcams, digital camcorder, wrist watches, game consoles, smart home appliances, including smart televisions and refrigerators, cars, smart glasses, eBook readers, etc. The transfer of image data to the ICD can include any method suitable including but not limited to direct streaming over a wireless or hard-wired connection as well as using a storage device such as a hard drive or a memory card or cloud storage. In some embodiments, the biometric sensor devices 106 indirectly provide data to the computing device 102. For example, the biometric sensor devices 106 may include a patient's own digital camera or a digital imaging device in the possession of any party, which may upload imagery to, e.g., a storage platform such as a cloud service for provision to the computing device 102 and storage system 104. Although examples using cameras capturing image data are provided herein, the biometric sensor devices 106 can include and use any combination of data acquisition devices capturing any combination of data without departing from the scope of the present disclosure.

In some embodiments, the system 100 can include an interface delivery server (IDS) 108. The IDS 108 can be designed to facilitate a connection between a biometric sensor device 106 and a computing device 102. In some embodiments, the IDS 108 includes a predictive load balancer (PLB) 110 that determines the most suitable computing device 102 within a cluster of computing devices 102. In one example, the PLB 110 can determine the most suitable computing devices 102 by tracking recent data deliveries and maintaining a session state for different client devices, so that data from the same client is regularly forwarded to the same computing devices 102 in a work server cluster. This serves to limit the repeated central shared memory access requirements. The ICD can generate an interface (e.g., webpage, app, etc.) that directly connects the biometric sensor devices 106 to the computing device(s) 102 determined to be most suitable by the PLB 110. This configuration may be used for establishing connections between clients and servers. For example, the biometric sensor devices 106 can be client devices, the computing devices 102 can be work servers, and the IDS 108 can handle negotiations to connect the client devices (biometric sensor devices 106) with the work servers (computing devices 102).

In some embodiments, the computing devices 102, 104, 106, 108 can be configured to establish a connection and communicate over the telecommunication network(s) 112 to carry out aspects of the present disclosure. The telecommunication network(s) 112 can include any combination of known networks. For example, the telecommunication network(s) 112 may be any combination of a mobile network, WAN, LAN, or other type of network. The telecommunication network(s) 112 can be used to exchange data between the computing devices 102, 104, 106, 108 exchange data with the storage system 104, and/or to collect data from additional sources.

In operation, the system 100 of the present disclosure can be designed to create a fully automated biometric monitoring system based on AI-enhanced computer vision alone, it can also be supplemented with other non-visual data sensor feeds, or it can also be supplemented with other non-visual data sensor feeds. This technical improvement can be realized by implementing a unique combination of processing stages, enhanced with new brain-inspired AI algorithms, acting in concert to make measurements fully automated without requiring any attendance or attention from operators, or even the patients under measurement.

Figure 2:
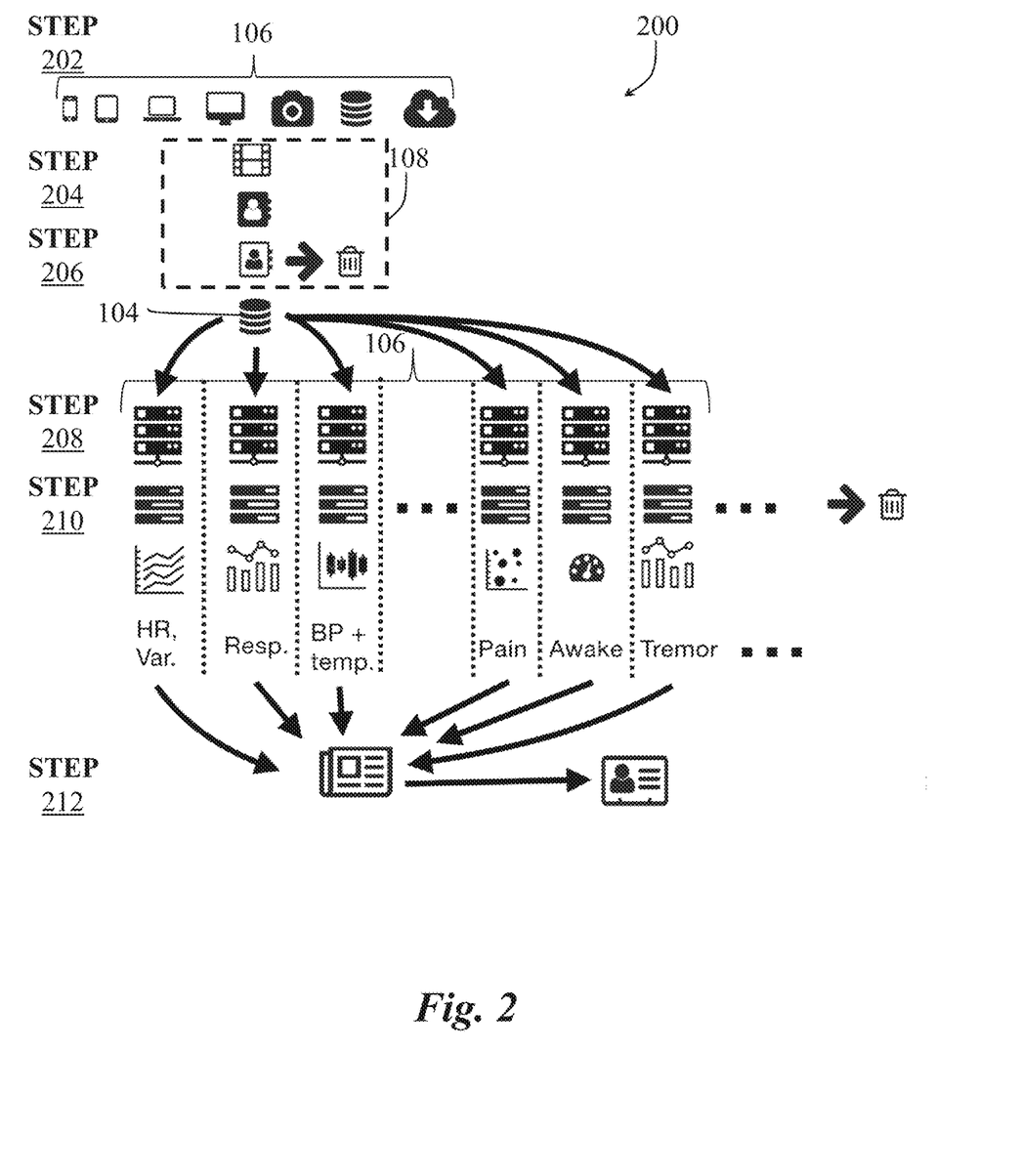
FIG. 2 is a diagram depicting a process of performing biometric analysis in accordance with the present disclosure.

Referring to FIG. 2, an example multi-stage process 200 for implementation of by the system 100 in accordance with the present disclosure is depicted. The process 200 is broken into a processing steps, which when used in combination result in a fully automated biometric monitoring process. Initially, client-server sessions are initiated between the biometric sensor devices 106 and the computing device(s) 102, for example, by the IDS 108. When a session is initiated, for example, with a ping to a central control server. The central control server can be any one of the computing devices 102 or it can be a separate dedicated control server. Regardless, in some embodiments, the control server can be designed to handle the allocation of tasks over the entire cluster of computing devices 102 and can also manage all the image preprocessing such as scaling and image conversion. In some embodiments, the control server can also create the subsidiary tasks that are handed off to the other individual pipelines and stages. For example, the control server can specify a specific queue of biometric data processing steps to be performed on an incoming video feed, and assign each biometric sensing task to different processing pipelines, each pipeline thread working on either a single processor in parallel, or farmed out to other computing device 102 (e.g., working servers) operating in a parallel cluster. Each processing pipeline can be tasked to process one individual biometric reading, (e.g., one thread for heart rate detection, another thread for respiration rate detection, and a third for blood pressure measurement, etc.) all in parallel. In some embodiments, each of the separate pipelines for each different biometric metrics (e.g., heart rate, respiration, etc.) can be executed by a single computing device 104, for example using parallel processing threads, separate computing devices 104 can be used for each pipeline, or a combination thereof.

At step 202, image data is captured by one or more biometric sensor device 106 for image stream preparation. The image data can include any combination of individually captured images and/or a constant stream of image data. For example, the control server can determine which image data can be a video stream. The image stream preparation can be implemented by which combination of the biometric sensor devices 106 and the computing devices 102. During image stream preparation, individual frames can be extracted from the captured image data received from the biometric sensor devices 106.

At step 204, the image data is analyzed for face location and video masking is performed. In some embodiments, the system 100 can use neural network face detection algorithms to identify where in the streaming image data a face is located. Once the face is identified, the location within the image data can be saved to the shared storage system 104. In some embodiments, with the location of a face identified, the system 100 can use a face masking algorithm that uses the boundary markers of the face detection algorithm that uses the boundary markers of the face detection algorithm to precisely and continuously identify, cut out, and register a region of interest around the face. The region cut out around the face, can include the face itself and a predetermined area around the face. This precisely cut mask of the face allows the vital sign signal extraction stage to precisely read minute facial variations in color (e.g., flush face, lack of color, yellow coloring, etc.) and motion (e.g., flaring nostrils, eye twitch, etc.), and patterns of color and motion from signal with minimal corruption from ambient image effects, motion artifacts or visual background noise. In some embodiments, the streaming image data can be segmented in five-second sequences of video. Thereafter, the sequences of video can be encrypted and uploaded from biometric sensor devices 106 to the computing device(s) 102, which house the majority of the processing infrastructure. Although five-second segments are used in the example provided in the discussion related to FIG. 2, any combination of segment lengths can be used without departing from the scope of the present invention.

At step 206, the face video segments from step 202 are received by the computing device(s) 102 for facial recognition processing. A wide variety of facial recognition algorithms can be applicable to this step of processing, where example embodiments are described in greater detail below. In some embodiments, during facial recognition, the computing device(s) 102 integrate continued bias detection that is used to tune the training sets and system performance on an ongoing basis to reflect the demographics, ethnicities, skin tones, etc. of a specific community where the image data is being obtained. The computing device(s) 102 can also use a clustering algorithm to determine most likely clusters of faces and transforming each the clusters into a label. A label, in this embodiment, can be an arbitrary semantic tag used to identify a particular cluster, i.e. "dark-skinned males," or "light skinned Asian females," or "elderly" or "child."

Thereafter, the computing device(s) 102 can classify each new image into the labels. For example, the computing device(s) 102 may employ a machine learning model including one or more classifiers, such as, e.g., a convolutional neural network, k-nearest neighbor, ensemble trees, an auto-encoder, or other classifiers. In some embodiments, each of the labels can have an initial probability calculated based on the relative size of the cluster and if the label probability moves outside of a statistical range for new images the computing device(s) 102 can generate an alert about this bias. The alert provides the system 100 with the ability to identify the need rebalance the training method to compensate for the bias, with the goal of approaching the theoretical performance limits in actual service deployments.

Continuing with step 206, the results of the facial recognition process, (i.e., the patient's characteristic facial features as described in a numerical vector), are compared to those of the facial images stored in a library of consenting participant records (e.g., within the storage system 110) to determine if the face from the processed image data corresponds to a preexisting face stored within the system 100. The comparison is performed to determine if the located face within the video segments belongs to a participant who consented to have their biometric data recorded. If the comparison does not find a match within the consenting participant records, the facial recognition video segment is deleted and all processing stops with no further computation. If the comparison does find a match within the consenting participant records, further analysis is authorized and the video segment is passed to the next step. In some embodiments, when facial recognition within a video segment is matched with the consenting participant records, the face may be tracked and all images with this face are tokenized and marked safe for continued processing. If multiple faces appear in a video segment, each of the recognized faces (e.g., faces that match a face in the consenting participant records) can be tracked and processed and no other facial video masking, capturing, or processing can occur for unidentified faces (e.g., faces that do not match faces in the consenting participant records).

In some embodiments, step 208 can include a data triage and shared memory stage. In the data triage and shared memory stage, the processed video segments can be first stored in a scalable shared memory data store that is accessible to all computing devices 102 acting as working servers in that shared memory cluster. Then a high-level video and ancillary data analysis system, based on a deep learning structured activity analyzer network, determines what is the rough high level content of the video segment, (for example, "facial video," or "full-body walking video") and dispatches the categorized and triaged video segment by content type to the appropriate processing clusters of computing devices 102 that work on that particular type of data. For example, "Facial Video" would be automatically dispatched to the processing cluster of computing devices 102 that can analyze facial imagery to automatically extract heart rate, respiration, and blood pressure, while "Full-body Walking Video" would be dispatched to a cluster of computing devices 102 that processes kinematics and dynamics of the gait and motor control to assess motor control injuries, deficits and disease, as well as physical energy expenditure.

At step 210, additional biometric data processing is performed on the image data captured in step 202 and authorized in step 204. In some embodiments, the biometric data processing includes applying the five-second facial video segments to a plurality of pipelines, each specifically designed for a particular biometric metric, etc. For example, heart rate can have its own pipeline process running in parallel with other biometric metric pipelines, as shown in FIG. 2. Within each of the pipelines, several stages of signal conditioning, de-trending, and de-noising algorithms, including a neuroscience-inspired algorithm, can be applied to the five-second facial video segments. One of more computer devices 102 within the system 100 can operate independently and be responsible for performing the processing steps for each of the pipelines. A pipeline can be created for any combination of biometrics that can be monitored and/or tracked using image data. Examples of the pipelines can include processes for monitoring heart rate, heart rate, respiration, blood pressure, temperature, pain, consciousness status, tremors, etc.

For a heart rate and heart rate variability measurement pipeline, three steps can be used to extract the final biometric signals from an image stream. The first step can use a deep learning-trained neural network modeled on the human retina that produces a complex nonlinear summation of the masked facial image RGB and IR (if available) channels that reduces each facially masked image in a stream to a single float value in the closed interval [0, 1] forming the equivalent of a raw Photo Plethysmographic (PPG) signal, such as those generated by an FDA approved Pulse Oximeter. This step can also serve to suppress confounding motion artifacts and the effect of moving lips during speech, eye-blinks, etc. The second step can de-trend and smooth the raw signal using noise reduction signal processing methods. During this process, the raw signal can be saved to a participant's data record, along with the fully processed version of the signal from the second step. The third step can be used to estimate the heart rate using an advance peak-detection algorithm on the smoothed and processed signals to measure the distance in milliseconds between each beat. This also enables the system to be able to estimate the variability of the signal over time.

For a respiration measurement pipeline, three steps can be used to analyze the incoming masked facial images for subtle color changes that indicate variations of blood oxygenation and performs a neural deep-learning non-linear summation to achieve super-resolution detection of the micro-motions of the head, facial features, and shoulders to generate its single variable estimate of respiration rate. The use of deep-learning based super-resolution algorithms architected after the mass-action distributed processing algorithms can describe how neurons in the human retina operate despite individually being very slow and noisy and imprecise in their signal transduction. The deep-learning algorithms can be used in aggregate and when using a complex nonlinear summation tuned from actual sensory data, they can share processing roles over a large distribution of neurons to achieve much higher accuracy in aggregate than any individual neural processor could manage.

The process performs a linear summation enhanced by the nonlinear activation functions and weight tunings based on repeated training intervals analyzing and measuring error rates of actual sample data. In some embodiments, the primary class of architectures used to learn the nonlinear signal and noise characteristics can be based on deep learning systems that leverage Generative Adversarial Network (GAN) system architectures to explore and optimize the signal filters, including autoregressive noise reduction and other similar architectures. The present disclosure uses this same distributed processing and signal averaging technique to achieve super-resolution even with limited precision sensors, such as consumer grade CMOS imaging cameras. The result is that these AI-enhanced signal analysis algorithms can demonstrate signal-to-noise ratio performance that is roughly 5 dB better than any competing solution. This extra signal detection capability allows even normal consumer grade video cameras to detect smaller signals hidden in more noise than any competing technology, as shown in FIGS. 3A and 3B.

Figure 3A:
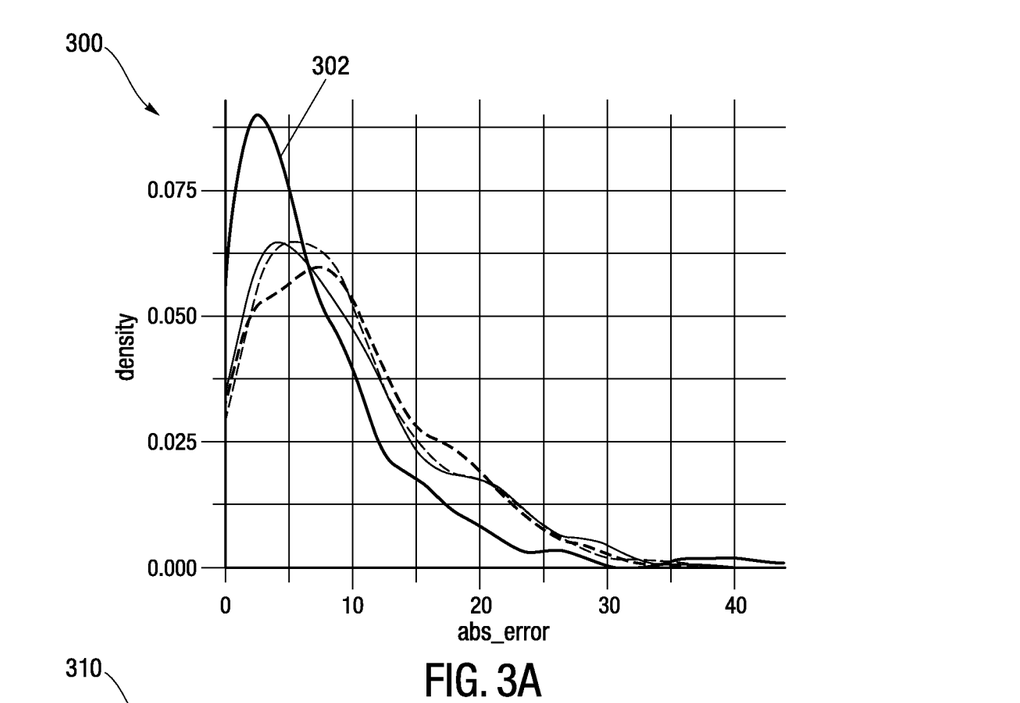
FIGS. 3A and 3B are histograms showing system of the methods in accordance with the present disclosure.
Figure 3B:
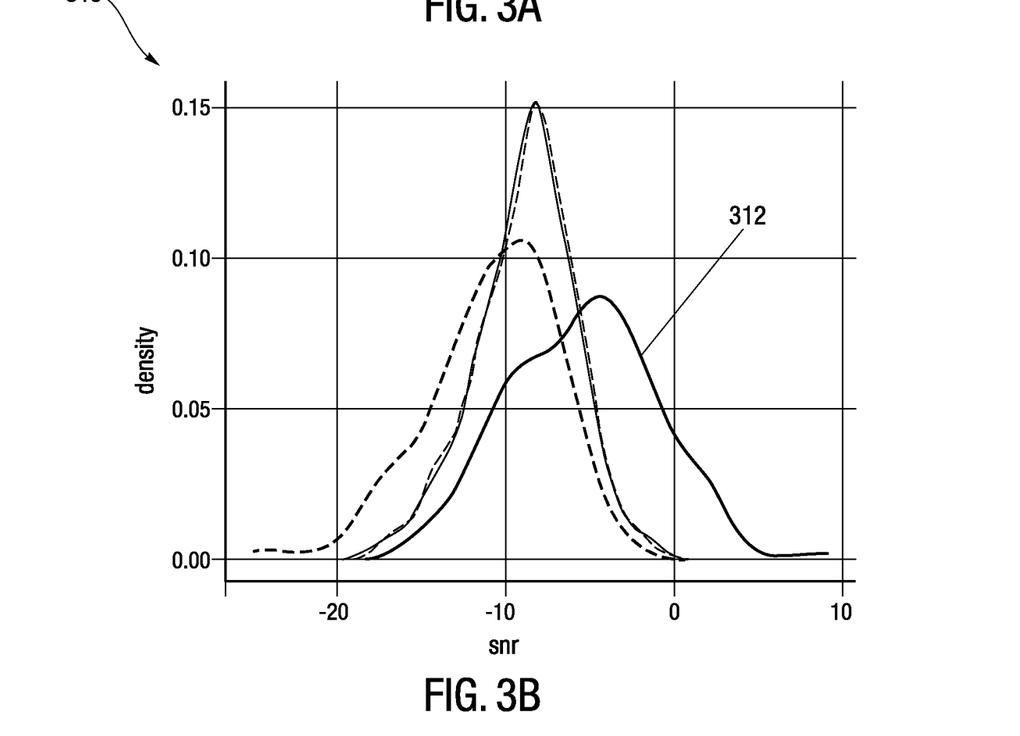

Referring to FIGS. 3A and 3B highlight how the AI enhanced biometric sensor devices 106 can detect signals that would otherwise be lost in noise. In particular, FIGS. 3A and 3B show the total mean squared error and signal to noise ratio using the system of the present disclosure outperforms conventional systems. FIG. 3A depicts a histogram 300 of the measurement errors in heart rate estimation of the system of the present disclosure (reflected in line 302), versus the top three state-of-the-art computer vision heart rate measurement systems using a publicly available participant records, where the present disclosure reduces the average absolute error by roughly 50%, a dramatic improvement. FIG. 3B depicts a histogram 310 of system performance on the same database and state-of-the-art competition, where the system of the present disclosure (reflected in line 312) demonstrates as roughly 5 dB Signal-to-noise rate improvement over conventional systems.

Continuing with FIG. 2, at step 210, signal quality estimation is performed on the data provided within the pipeline(s) from step 208. For example, once the heart rate and heart rate variability measurement pipeline resulting signals from step 206 can be used for a signal quality estimation. The signal quality estimation is based on how the human visual cortex processes imagery. For example, by magnifying and amplifying expected signals, or signals that have been seen repeatedly in the past, while concurrently, suppressing the gain on the rest of the incoming signal as noise, the signal quality estimation may exceed physical limitations of an imaging sensor itself. This is accomplished through the development of specialized signal templates in a neural format learned from measured data using a multiplicity of learning algorithms, In some embodiments, these neural signal and noise detection filters can be developed through a series of autoregressive and variational autoencoder methods that repeatedly sample tagged biometric sensor data that is both clean, and corrupted with known levels of noise, to determine the unique signal characteristics of data that is representative of real-world measurement conditions. In operation each neural signal versus noise filter for each individual biometric measurement can be compared with the incoming data as a post-measurement filter, to assess the quality of each and every measurement. In other words, each individually measured biometric signal has a uniquely paired assessment of its signal to noise ratio or measurement quality.

For example, for the heart rate measurement pipeline, a neural processor, using repeated exposure to sample example high quality PPG signals, is trained to detect the typical PPG signal pattern in a de-trended signal. To accomplish this, the neural processor may employ a complex deep-learning based nonlinear convolutional filter that can account for significant variations in the signal template. However, other signal template matching algorithms are also contemplated for matching the PPG signals to typical PPG signals.

In some embodiments, where the de-trended signal is not found to contain the expected signal pattern or detects too many patterns that deviate statistically significantly from the mean template patterns, then the signal quality is low. For example, for each measurement in this heart-rate pipeline, there may be a matched pair assessment of the signal-to-noise level for the specific heart rate type signals this pipeline was trained to detect. If a signal has low quality it is discarded for the estimation of heart rate and variability. As such, for each measurement in this pipeline, there is a matched pair assessment of the signal-to-noise level for the specific heart rate type signals this pipeline was trained to detect.

The resulting signal quality estimation allows the system 100 to assign thresholds of acceptability, where signals that fall below the SNR threshold are discarded, and only those which meet the accuracy requirements (for example the 10% accuracy requirement for FDA approval of vital sign measurements) are passed to step 212 for recording and rendering on observation and monitoring panels or client-side user interfaces.

At step 212 perform analysis of the signal quality estimation to assess the quality of each individual measurement. In some embodiments, continuous quality measurements can be taken, for example, every five seconds. The continuous quality measurements provide application developers with the ability to dynamically choose, and dial up or down, the volume of data versus the accuracy of the aggregate measurements. For example, if the accuracy requirement set by the FDA for heart rate measurements is 10%, all measurements can be accepted to generate an average absolute error rate in the current embodiment that is less than 10%. But for super-high-fidelity applications, such as neonatal surgery, the system 100 accuracy threshold can be set to a more stringent SNR minimum, so that high-variance measurements are rejected, and only those with the minimum SNR level are passed, resulting in accuracies better than 2%.

In one example experiment, when the system 100 parameters were set to FDA approval level accuracy requirements, the system 100 classified 552 of the total 1,357 measurements as achieving the sufficient quality requirement of average accuracy of 93% with a MAE<4.9 and a SD<5.2. This is comparable with the already FDA approved Apple watch, a contact based PPG monitor measured to have an accuracy of 92%. When set to more stringent threshold levels ~95% reducing MAE to <3.8 and SD to <2.8 the number of valid samples meeting the tighter requirements drops to 268, yet still more than enough to compete with current commercial wired-contact based systems that generate a single time averaged heart rate measurement every 30 seconds.

In other words, when set to the more stringent signal quality threshold, the system 100 of the present disclosure can be tuned to perform comparably, or if necessary substantially better than, the current generation of commercially available FDA approved wired sensors for heart rate and respiration. These performance metrics can be achieved while also offering substantial advantages that attend the non-contact computer vision measurement modality, such as eliminating infection risk, allowing patient mobility even under measurement, and the complete automation of formerly manual tasks.

Figure 4A:
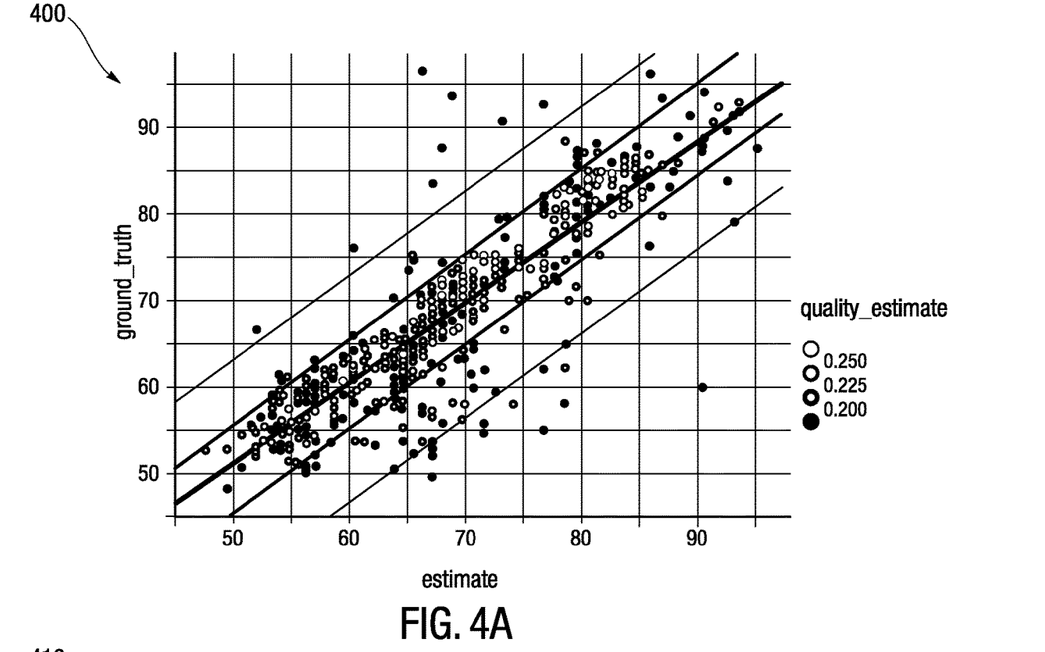
FIGS. 4A and 4B are experiment results comparing the conventional devices versus biometric sensor devices in accordance with the present disclosure.
Figure 4B:
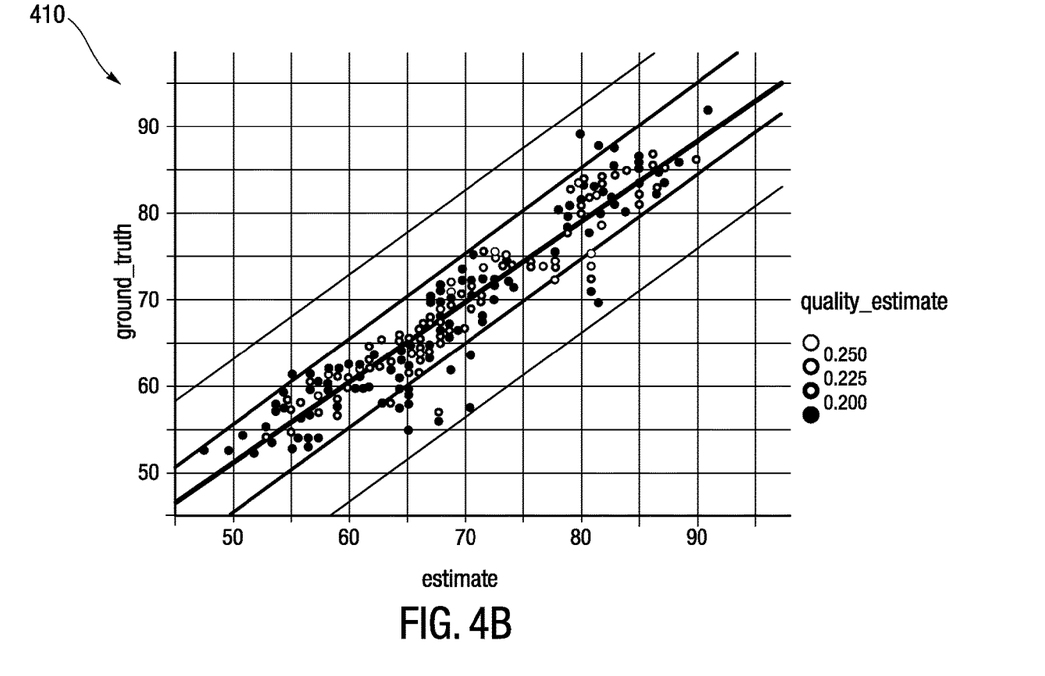

Referring to FIGS. 4A and 4B highlight how the AI enhanced biometric sensor devices 106 can assess and measure signal quality. In particular, FIGS. 4A and 4B show experiment results comparing the biometric sensor devices 106 versus conventional devices. FIG. 4A shows a graph 400 showing results for ground truth measurements from FDA-approved medical sensor (y-axis) versus the biometric sensor devices 106 of the present disclosure (x-axis). The level of darkness of each data point shows the AI based assessment of signal quality for each measurement, roughly equivalent to a signal-to-noise ratio (SNR), where lighter is better. In the graph 400, the SNR quality threshold for the experiment is set to only record data within the minimum FDA required range of ~10% accuracy.

FIG. 4B shows a graph 410 showing results for the same experiment used to chart graph 400 but with the data measurement quality threshold set to only accept data using a more stringent required threshold of mean absolute error acceptability<3.8 bpm and Standard Deviation <2.8 bpm, an accuracy rate of ~%7.5. As shown in graph 410, the combined effect of AI-enhanced sensing, and signal quality assessment together is dramatic because not only does the system improve signal quality absolutely by about 5 dB, but lower quality signals (those measurements that fall to the left, below a tunable threshold can be discarded, so the total improvement in overall signal measurement quality can top 10 dB, to generate more than a 10× signal quality improvement over state of the art). It is this improved tolerance of noise that allows the present disclosure to operate using even limited precision consumer grade camera parts in support of telemedicine applications that operate over most consumer grade mobile phones, tablets, and computers already distributed in the commercial marketplace. In this telemedicine application, the enabling capability is that the new signal versus noise detection algorithms treat lower precision sample data as a simple structured noise that can be filtered, and further, measurements where the sensor or subject, or lighting or background changes are simply automatically discarded.

Continuing with FIG. 2, at step 214 the results of steps 202-212 are stored within a participant's data record. For example, when a biometric data signal is validated for an authenticated consenting participant, the system 100 automatically logs the results to their electronic record. The data can then be relayed to the appropriate reviews. For example, the data record can be shared with a supervisory, doctor and nurse review stations for multiple patient oversight, and directly back to client device screens for user interface rendering.

Figure 5:
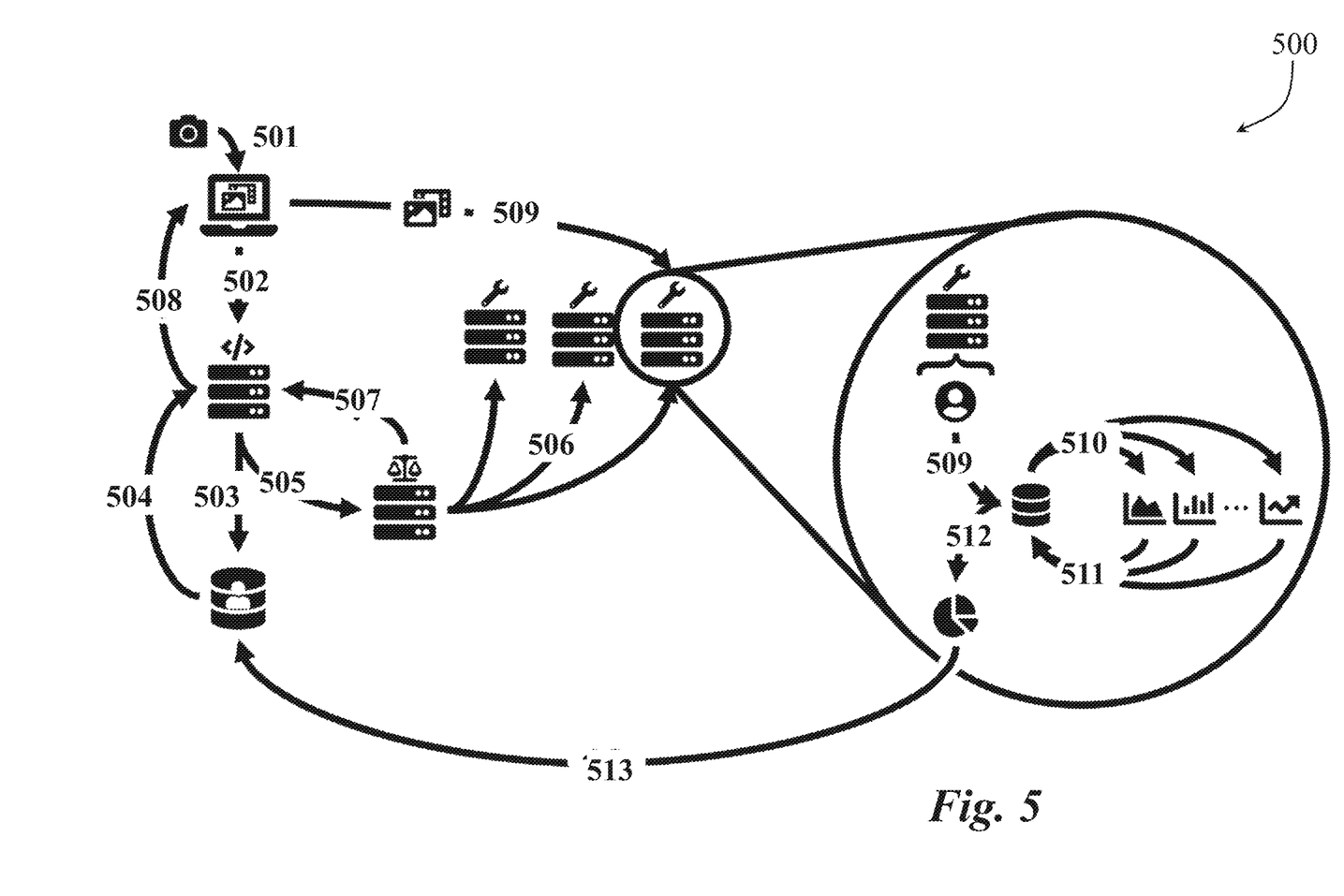
FIG. 5 is a diagram depicting a process of performing biometric analysis in accordance with the present disclosure.

Referring to FIG. 5 an example process 500 for implementing the present disclosure is provided. FIG. 5 depicts the process 500 for transforming image data captured from cameras connected to biometric sensor devices 106 to biometric data. The process 500 can be used to derive biometric data from the image data without the aid of other biometric devices attached to the subject.

At step 501 image data received from the cameras can be transferred to the biometric sensor devices 106. The transfer from the camera to the biometric sensor devices 106 can include any type of data transfer, for example, wireless, external wiring, internal wiring, etc. Similarly, any combination of cameras can be connected to or otherwise part of the biometric sensor devices 106 can provide the image data to the biometric sensor devices 106. For example, the biometric sensor devices 106 can be a smartphone with an embedded camera designed to capture images and video for storage on the local storage of the smartphone. The biometric sensor devices 106 can store the image data locally and/or remotely, for example in local memory and cloud storage.

At step 502 the biometric sensor devices 106 can request an interface from an interface delivery server (IDS) 108 to establish a connection with one or more computing devices 102 to perform analysis of the image data. The interface can take multiple forms including but not limited to an HTML based website or precompiled code executable in an app on the biometric sensor devices 106.

At step 503 The IDS 108 can connect to a storage system 104 maintaining a user database associated with the present disclosure. For example, the IDS 108 can connect to a central repository that includes a user database that maintains user account settings and records. Thereafter, the IDS 108 can request relevant user information from the user database to ensure secure login by the credentials provided by the biometric sensor devices 106.

At step 504, in response to receiving the request from the IDS 108, the storage system 104 can provide the appropriate user data to the IDS 108. After the IDS 108 retrieves the user data, it can generate a secure token to in a authentication process with one or more computing devices 102. In this example the computing devices 102 can be worker servers operating as part of a server cluster, as shown in FIG. 5. The computing devices 102 acting as work serves can provide the functionality to transform the recorded images, chunks, or video streams called Frame Data (FD) into biometric data.

At step 505 the IDS 108 can request information about which/how many computing devices 102 are available within the server cluster from the PLB 110. In some embodiments, the PLB 110 can maintain a prioritized queue of records as what computing devices 102 are available by relative load, and which biometric sensor devices 106 have submitted data records to which computing devices 102 that might have all necessary data for that user already in memory, in order to select the optimal match.

At step 506 The PLB 110 can predict future workload on the cluster of computing devices 102. Based on the future workload, the PLB 110 can determine the most suitable computing device 102 within the cluster for processing the image data (e.g., process 200 of FIG. 2) from the biometric sensor devices 106. In some embodiments, the PLB 110 can predict the future workload by analyzing historical log records of specific user access patterns (e.g., from the participant records) and timing to determine the most suitable computing device 102 that can most efficiently address that user and the biometric sensor devices 106 processing needs with minimum network and shared memory load.

At step 507 The PLB returns required details for providing an interface for communicating with the most suitable computing device 102 to perform the analysis. At step 508 the IDS 108 compiles the interface based on the received required details for the computing device 102 and the user information and returns the interface to the biometric sensor device 106. The biometric sensor device 106 can use the received interface to directly connects to the allocated computing device 102, for example, as part of a client-server relationship.

At step 509 The biometric sensor device 106 device uses the generated interface to transfer the Frame Data (e.g., image data) to the computing device 102 for processing. The biometric sensor devices 106 can transmit either each recorded image individually in an intermittent stream, or streams of a subset of the recorded images as a stream of chunks of video—either as raw or uncompressed data in any suitable form of encoding (e.g., as a video or stream of individual pictures, or subset regions of interest clipped from whole video, or the complete video stream) to the computing device 102 over the established secure connection created by the interface.

At step 510 the computing device 102 can prepare the frame data into individual frames and process each frame processed individually in parallel pipelines and blocking free. As part of the processing, the computing device 102 can use a checking process to analyzes each frame of the fame data stream to determine if the captured image includes a face of a willing participant (e.g., someone enrolled to use a service provided by the present disclosure). If the frame contains the face of a willing participant the computing device 102 can initiate an asynchronous non-blocking process chain by adding the frame data to the local shared memory, accessible only within the single cluster of computing devices 102 that are associated with that shared memory. Thereafter, the frame checking process in the control server can generate tasks for each process in the chain as appropriate to that particular type of data. In the shared memory and data triage stage, the control server can determine the rough content of the visual and ancillary data to dispatch the proper processing chain for that data type. For example, each process within the chain can be responsible for determining a different biometric metric, such as, heart rate, respiration, blood pressure, temperature, pain, tremors, etc.

At step 511 each process in this chain can be a pre-processing step such as masking the users face or an analyzer (e.g., calculating heart rate). All processes can be independent and can be run in parallel by a single selected computing device 102, virtual machines created by the selected computing device 102, or a combination of computing devices 102. Processes performed by the pipelines can include image stream preparation and session initiation, face detection and location, face recognition, authentication and access control, face masking, video telemetry and relay to the central processing servers, video signal conditioning and de-trending, and noise removal, vital sign and biometric signal extraction and analysis, vital sign signal processing, measurement quality assessment, data storage, security, and persistence/archiving.

In some embodiments, inter-process communication is ensured through the shared memory system. At step 512 each process shares results through the shared memory. In some embodiments, the shared memory can be stored on a single computing device 102 where all the processing pipeline threads and processes operate within or on a single machine memory mounted in a larger computer cluster with a high-bandwidth network bus to access the single scaled shared memory by all computing devices 102 within a cluster. In some embodiments, a single shared memory can be partitioned across multiple computing devices 102 within a cluster where portions of the larger database are stored in each computing device 102. In some embodiments, only the authenticated computing devices 102 in the single processing cluster can access the shared memory associated with that cluster. The processes running on the computing devices 102 with that cluster can use all the image information in the shared memory including any results or data from the other processes that operate on the shared data and subsequently store results in the shared memory.

Each pipeline module and stage can operate directly in shared memory in a networked architecture where any pipeline module can be located anywhere between the biometric sensor device 106 client and the computing devices 102, or completely co-located on a single remote or centrally located cloud device At step 513 a wrap up process runs once the individual processes have finished their work. In some embodiments, the wrap up process can take all the results stored in shared memory and persist the results within the storage system 104 (e.g. cloud storage, local hard drive, etc.) and discard any intermediate scratch results or data. In some embodiments, all data from shared memory can be specified data to be deposited within the permanent participant records. Depending on the type of information being stored, the data can be deidentified, encrypted, etc. to be in compliance with the appropriate regulations, for example, HIPAA and GDPR.

Using the processes 200 and 500 discussed with respect to FIGS. 2 and 5, receptively, the system 100 can be used to perform wireless biometric monitoring using cameras as ambient biometric sensors. The ambient biometric sensors can be used to track any combination of biometrics such as for example, heart rate, heart rate variability, respiration rate, and blood pressure, but wide range of biometric measurements are possible using the same core architecture including facial expressions, pain levels, movement disorders, drug efficacy, attention disorders, wakefulness, jaundice detection, etc. This provides a way for physicians to track and monitor consenting patient's biometrics, passively, removably, and without the need to connect sensors to the patients using any cameras that may be near a patient (e.g., participant). The present disclosure can also be used to perform fully or semi-automated diagnosing of a patient from simple video, for example, an auto-doctor that can check a patient out through whatever screen and camera a patient might be in front of patient. In such implementations, consenting patients need only wander into the field of view of an ambient biometric sensor, and with no attention at all and no attending nurses or physicians, their vital signs are automatically measured and recorded to their respective user health records.

Figure 6:
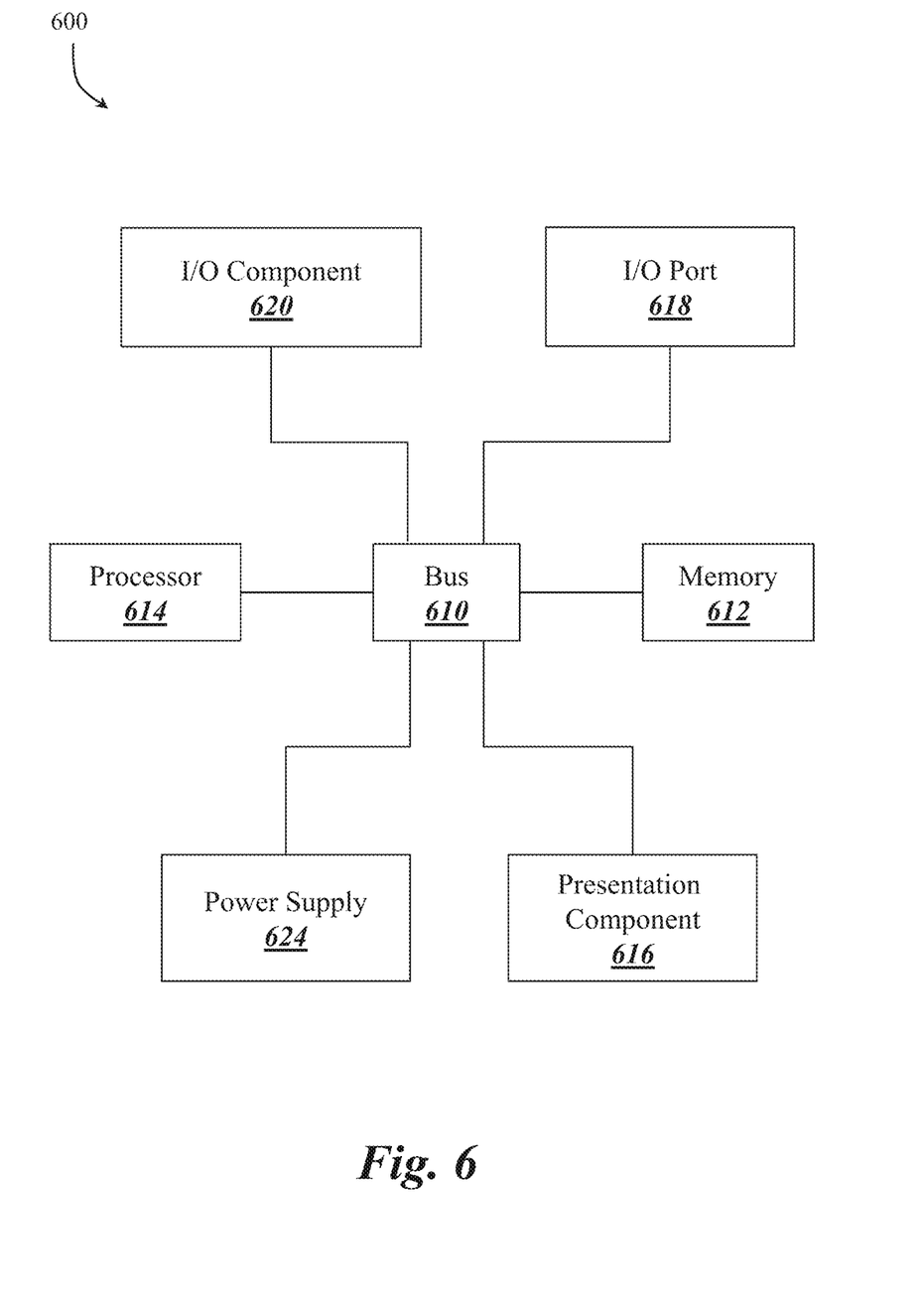
FIG. 6 is a diagrammatic illustration of a high-level architecture for implementing processes in accordance with the present disclosure.

Any suitable computing device can be used to implement the computing devices 102, 104, 106, 108 and methods/functionality described herein and be converted to a specific system for performing the operations and features described herein through modification of hardware, software, and firmware, in a manner significantly more than mere execution of software on a generic computing device, as would be appreciated by those of skill in the art. One illustrative example of such a computing device 600 is depicted in FIG. 6. The computing device 600 is merely an illustrative example of a suitable computing environment and in no way limits the scope of the present disclosure. A "computing device," as represented by FIG. 6, can include a "workstation," a "server," a "laptop," a "desktop," a "hand-held device," a "mobile device," a "tablet computer," or other computing devices, as would be understood by those of skill in the art. Given that the computing device 600 is depicted for illustrative purposes, embodiments of the present disclosure may utilize any number of computing devices 600 in any number of different ways to implement a single embodiment of the present disclosure. Accordingly, embodiments of the present disclosure are not limited to a single computing device 600, as would be appreciated by one with skill in the art, nor are they limited to a single type of implementation or configuration of the example computing device 600.

The computing device 600 can include a bus 610 that can be coupled to one or more of the following illustrative components, directly or indirectly: a memory 612, one or more processors 614, one or more presentation components 616, input/output ports 618, input/output components 620, and a power supply 624. One of skill in the art will appreciate that the bus 610 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 6 is merely illustrative of an exemplary computing device that can be used to implement one or more embodiments of the present disclosure, and in no way limits the invention.

The computing device 600 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 600.

The memory 612 can include computer-storage media in the form of volatile and/or nonvolatile memory. The memory 612 may be removable, non-removable, or any combination thereof. Exemplary hardware devices are devices such as hard drives, solid-state memory, optical-disc drives, and the like. The computing device 600 can include one or more processors that read data from components such as the memory 612, the various I/O components 616, etc. Presentation component(s) 616 present data indications to a user or other device. Exemplary presentation components include a display device, speaker, printing component, vibrating component, etc.

The I/O ports 618 can enable the computing device 600 to be logically coupled to other devices, such as I/O components 620. Some of the I/O components 620 can be built into the computing device 600. Examples of such I/O components 620 include a microphone, joystick, recording device, game pad, satellite dish, scanner, printer, wireless device, networking device, and the like.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion may be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure may vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present disclosure be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method for fully-automated contact-less biometric measurement comprising:

receiving, by at least one processor, a set of image frames produced by one or more biometric sensor devices including at least one digital image capture device;

extracting, by the at least one processor, a set of patient face images associated with a user captured by one or more frames of the set of image frames;

determining, by the at least one processor, a patient identity of the user associated with the set of patient face images of the one or more frames of the set of image frames using a facial recognition machine learning model;

storing, by the at least one processor, the set of patient face images in a shared memory system with shared access by a plurality of independent biometric data processing pipelines;

determining, by the at least one processor, one or more biometric measurements of the user based on the set of patient face images in the shared memory system, each of the one or more biometric measurements being determined with an independent biometric data processing pipeline of the plurality of independent biometric data processing pipelines with the shared access to the shared memory system for inter-process communication;

wherein each of the one or more biometric measurements comprises a distinct health-related metric of the user;

exporting, by the at least one processor, the one or more biometric measurements to a user database; and displaying, by the at least one processor, a selected set of the one or more biometric measurements on a screen of a user computing device in response to a user selection.

2. The method of claim 1, further comprising determining, by the at least one processor, a consent status associated with the patient identity indicating whether consent for biometric analysis exists.

3. The method of claim 1, further comprising balancing, by the at least one processor, each independent biometric data processing pipeline across a plurality of worker servers using a predictive load balancer.

4. The method of claim 1, further comprising determining, by the at least one processor, a neural biometric data signal for each set of patient face images independently with each independent biometric data processing pipeline using a respective super-resolution neural network.

5. The method of claim 1, further comprising determining, by the at least one processor, a quality measurement of a respective one or more biometric measurement in each independent biometric data measurement pipeline using a respective signal template neural network of a one or more signal template neural networks.

6. The method of claim 1, wherein the set of image frames comprises frames of one or more videos, each of the one or more videos comprising five seconds in duration.

7. The method of claim 1, further comprising sharing, by the at least one processor, results between each of the one or more independent biometric data measurement pipelines via the shared memory system;

wherein the results comprise one or more of the following:

the respective one or more biometric measurements of the respective one or more independent biometric data measurement pipelines, a respective quality measurement of the respective one or more independent biometric data measurement pipelines, and a respective neural biometric data signal of the respective one or more independent biometric data measurement pipelines.

8. The method of claim 6, wherein the set of image frames comprises the frames of a user selected subset of the one or more videos.

9. A method for contact-less biometric measurement comprising:

receiving, by at least one processor, a stream of image frames produced by one or more biometric sensor devices including at least one internet capable device;

extracting, by the least one processor, frame data from the stream of image frames comprising a plurality of images;

determining, by the at least one processor, at least one worker server from a plurality of worker servers based on a future load prediction by a predictive load balancer;

communicating, by the at least one processor, the frame data from the at least one internet capable device to the at least one worker server;

extracting, by the at least one processor, a set of patient face images associated with a user captured by the frame data;

determining, by the at least one processor, a patient identity of the user associated with the set of patient face images of the frame data using a facial recognition machine learning model;

storing, by the at least one processor, the set of patient face images in a shared memory system with shared access by a plurality of independent biometric data processing pipelines;

determining, by the at least one processor, one or more biometric measurements based on the set of patient face images in the shared memory system, each of the one or more biometric measurements being determined with an independent biometric data processing pipeline of the plurality of independent biometric data processing pipelines with the shared access to the shared memory system for inter-process communication;

wherein each of the one or more biometric measurements comprises a distinct health-related metric of the user;

exporting, by the at least one processor, the one or more biometric measurements to a user database; and displaying, by the at least one processor, a selected set of the one or more biometric measurements on a screen of a user computing device in response to a user selection.

10. The method of claim 9, further comprising determining, by the at least one processor, a consent status associated with the patient identity indicating whether consent for biometric analysis exists.

11. The method of claim 9, further comprising balancing, by the at least one processor, each independent biometric data processing pipeline across a plurality of worker servers of the at least one worker server using the predictive load balancer.

12. The method of claim 9, further comprising determining, by the at least one processor, a neural biometric data signal for each set of patient face images independently with each independent biometric data processing pipeline using a respective super-resolution neural network.

13. The method of claim 9, further comprising determining, by the at least one processor, a quality measurement of a respective one or more biometric measurement in each independent biometric data measurement pipeline using a respective signal template neural network of a one or more signal template neural networks.

14. The method of claim 9, wherein the stream of image frames comprises frames of one or more videos.

15. The method of claim 9, further comprising sharing, by the at least one processor, results between each of the one or more independent biometric data measurement pipelines via the shared memory system;

wherein the results comprise one or more of the following:

the respective one or more biometric measurements of the respective one or more independent biometric data measurement pipelines, a respective quality measurement of the respective one or more independent biometric data measurement pipelines, and a respective neural biometric data signal of the respective one or more independent biometric data measurement pipelines.

16. The method of claim 14, wherein the frame data comprises the frames of a user selected segment of the one or more videos.

17. The method of claim 16, wherein the user selected segment of the one or more videos comprises a selection of one or more segments each comprising 5 seconds in duration.

18. A system for contact-less biometric measurement comprising:
one or more internet connected devices configured to:
produce a stream of image frames produced by one or more biometric sensor devices including at least one internet capable device, and
extract frame data from the stream of image frames comprising a plurality of images;
a plurality of worker servers, each worker server comprising a respective at least one processor and a respective shared memory system;
a user database in communication with the plurality of worker servers and the one or more internet connected devices;
a predictive load balancer in communication with the plurality of worker servers and configured to determine at least one worker server from the plurality of worker servers based on a future load prediction;
an interface delivery server in communication with the plurality of worker servers, the predictive load balancer and the one or more internet connect devices, and configured to communicate the frame data from the at least one internet capable device to each of the predictive load balancer and the at least one worker server;
wherein the at least one processor of the at least one worker server is configured to:
extract a set of patient face images associated with a user captured by the frame data;
determine a patient identity of the user associated with the set of patient face images of the frame data using a facial recognition machine learning model;
store the set of patient face images in the shared memory system with shared access by a plurality of independent biometric data processing pipelines;
determine one or more biometric measurements based on the set of patient face images in the shared memory system, each of the one or more biometric measurements being determined with an independent biometric data processing pipeline of the plurality of independent biometric data processing pipelines with the shared access to the shared memory system for inter-process communication; and
wherein each of the one or more biometric measurements comprises a distinct health-related metric of the user;
export the one or more biometric measurements to the user database.

19. The system of claim 18, wherein the at least one processor of the at least one worker server is further configured to share results between each of the one or more independent biometric data measurement pipelines via the shared memory system;
wherein the results comprise one or more of the following:
the respective one or more biometric measurements of the respective one or more independent biometric data measurement pipelines,
a respective quality measurement of the respective one or more independent biometric data measurement pipelines, and
a respective neural biometric data signal of the respective one or more independent biometric data measurement pipelines.

20. The system of claim 18, wherein the interface delivery server is further configured to display a selected set of the one or more biometric measurements on a screen of the one or more internet connected devices in response to a user selection.

* * * * *